United States Patent
Glenn et al.

(10) Patent No.: US 6,225,640 B1
(45) Date of Patent: May 1, 2001

(54) METHOD FOR ELECTRICAL SHUNT DETECTION AND REMOVAL ON SEMICONDUCTORS

(75) Inventors: Gregory S. Glenn, Pacific Palisades; Michael L. Rupp, Reseda, both of CA (US)

(73) Assignee: Hughes Electronics Corporation, El Segundo, CA (US)

( * ) Notice: Subject to any disclaimer, the term of this patent is extended or adjusted under 35 U.S.C. 154(b) by 0 days.

(21) Appl. No.: 09/323,221

(22) Filed: May 19, 1999

(51) Int. Cl.[7] .......................... H01L 31/18; G01N 21/88
(52) U.S. Cl. ...................... 250/559.45; 136/29; 438/12
(58) Field of Search .................. 250/559.45–559.48; 205/656; 136/243, 244, 258, 290; 438/12

(56) References Cited

U.S. PATENT DOCUMENTS

| | | |
|---|---|---|
| 4,166,918 | 9/1979 | Nostrand et al. . |
| 4,543,171 | 9/1985 | Firester et al. . |
| 4,640,002 * | 2/1987 | Phillips et al. ...................... 136/290 |
| 4,749,454 | 6/1988 | Arya et al. . |
| 5,367,174 * | 11/1994 | Bazile et al. .................... 250/559.45 |

\* cited by examiner

Primary Examiner—Stephone B. Allen
(74) Attorney, Agent, or Firm—T. Gudmestad

(57) ABSTRACT

An improved method of detecting and removing a shunt from a photoelectric semiconductor device comprises the steps of characterizing the device by generated data or performance graph; forward biasing the device; producing electromagnetic radiation from the device; receiving the radiation; associating a contrast in radiation to the defect; and mechanically removing the defect, whereby the defect is removed in the absence of a step of applying a chemical to the defect to assist in removing the defect.

35 Claims, 4 Drawing Sheets

METHOD FOR ELECTRICAL SHUNT DETECTION AND REMOVAL ON SEMICONDUCTORS

BACKGROUND OF THE INVENTION

1. Field of the Invention

The present invention generally relates to shunt removal from semiconductor devices and, more particularly, to an improved method for detecting and then removing selected shunt(s) from a semiconductor device such as a photovoltaic cell.

2. Description of Related Art

The interest in photovoltaic (PV) cells has continued as concerns over pollution and limited resources have continued to grow. The continued interest has been in both terrestrial and space applications. In the non-terrestrial environment of outer space, the concern over limited power resources is a major one. This is because the need to increase the amount of power often increases the spacecraft mass. An increased mass can increase the cost of a launch more than linearly due to fuel costs. With the ready availability of solar energy in space for a spacecraft such as a satellite, the conversion of solar energy into electrical energy is an obvious choice. Increasing the efficiency of the solar conversion process can either reduce the spacecraft mass or allow more high value payload to be flown.

Irrespective of the application, and as with any energy generation system, efforts have been ongoing into increasing the output and/or efficiency of PV cells. One such effort to increase efficiency involves converting photon energy from a wider portion of the light energy spectrum. Multiple cells or layers having different energy bandgaps have been stacked so that each cell or layer can absorb a different part of the energy distribution in light. Multiple p-n (or n-p) junctions are formed to create a monolithic stacked multi-junction solar cell.

Efficiency in a monolithic cell PV device can be limited by the existence of defects in the cells themselves. One such defect is a "shunt," which can cause electrical degradation of the cell. A shunt provides a low-resistance path for a portion of the current flow. In a "short," there is virtually no resistance to the current flow. "Shunts" can be caused by foreign material introduced during the growth phase of constructing the PV cell or other type of semiconductor device by metal-organic vapor phase epitaxy (MOVPE) for example.

With the potential for defects to exist in the cell, electrical testing of the device has typically been used to determine if the device can provide useful performance. If several shunts exist, and/or if one significant shunt exists, the electrical degradation may be enough to warrant scrapping the device. In the context of photovoltaic cells, one scrapped cell may represent hundreds of dollars in materials and processing labor. The cost of scrapped cells has continued to increase as the cost of materials used in making the cells has increased. For example, the concern over efficiency in PV cells has created more interest in the use of germanium, gallium arsenide, indium phosphide, and gallium indium phosphide, which tend to be more efficient but also more expensive than their silicon predecessor. Indium phosphide, and phosphide semiconductors in general, have another advantage of being radiation resistant, which is of particular benefit in space applications. Yet, these more advantageous materials can only be expected to increase in cost over the next years.

In an apparent effort to reduce the amount of scrap, application of a reverse bias voltage and/or chemical etching has been used to remove shunts, thereby rendering the device useful. For example, U.S. Pat. No. 4,166,918 discloses a method of improving the performance of an amorphous silicon solar cell by applying a reverse bias current of sufficient magnitude to burn out electrical shorts and shunts, but at less than the breakdown voltage of the solar cell. Chemical etching, however, is not used in this application. One disadvantage to such method is that the application of a reverse bias to a gallium arsenide or similar type cell tends to increase the incidence of shorts or shunts. Another disadvantage is that conditions needed to burn out a severe shunt may damage the cell further.

U.S. Pat. No. 4,543,171 discloses a method of preferentially etching an exposed surface of a photodetector and applying a reverse-bias voltage. In so doing, the temperature of the exposed surface at the defect site increases so that an etchant can remove the defect. A similar method is disclosed in U.S. Pat. No. 4,749,454. The disadvantages in these methods are similar to those described above. Another disadvantage is that a defect may not be located in a position that is susceptible to exposure by the etchant. A further disadvantage is that exposure of the entire device to the etchant may cause damage and electrical degradation to other areas of the cell.

Also described in U.S. Pat. No. 4,543,171 is a method of defect removal that pre-existed such patent. In such pre-existing method, the device is placed under a reverse-bias voltage. The defect is located by means such as thermally sensitive liquid-crystal techniques or infrared-imaging techniques. After the defect is located and the bias removed, an acid etchant is locally applied to the cell to remove the defect. Again, however, a defect may not be located in a position that is susceptible to exposure by the etchant or too much of the cell may be damaged, since the process is not locally selective.

To better appreciate the limitations of the past methods of defect removal, it can be noted that when metal grids are used to collect electrons in a semiconductor, shunts can exist under the metal grids, as well as between them. For a small shunt that exists between metal grids, applying a reverse-bias voltage and/or chemical etchant may be adequate to remove the shunt. But for a shunt that exists under a metal grid (which can be 4 micrometers thick or thicker), applying a reverse-bias voltage of sufficient magnitude to remove semiconductor material (and thereby the shunt) from under the grid would likely degrade the cell further by driving metallic contaminants deeper into the junction, thus causing the cell to be rejected for use. Furthermore, a shunt under a metal grid would not be susceptible to exposure by a chemical etchant.

As can be seen, there is a need for a method of improving the performance of a semiconductor device, including a photovolaic cell, and minimizing the potential for having to scrap such device after it has been grown. Also needed is an improved method of detecting and then removing electrical defects from semiconductor devices, including multi-junction and/or single junction photovoltaic cells. Another need is for an improved method of selectively identifying which of a number of shunts require removal and then removing only those needed to be removed. An additional need is for a method of removing those shunts that exist under a metal grid. Yet a further need is for an improved method of removing shunts that are not susceptible to chemical removal. Also needed is improved apparatus to accomplish the above needs.

SUMMARY OF THE INVENTION

The present invention is directed to a method of improving the performance of a semiconductor device, including a photovolaic cell, and minimizing the potential for scrap material in growing such device. The present invention also provides an improved method of detecting and then removing electrical defects from semiconductor devices, including multi-junction and/or single junction photovoltaic cells. The improved method of the present invention also provides for selectively identifying which of a number of shunts require removal and then removing only those needed to be removed. The present method also provides for the removal of shunts that exist under a metal grid or others that are not susceptible to chemical removal. Improved apparatus is also provided by the present invention to accomplish the methods.

Specifically, the improved method of detecting and removing an electrical defect from a semiconductor device comprises the steps of producing electromagnetic radiation from the device; receiving the radiation; detecting a contrast in radiation; associating the contrast to the defect; and mechanically removing the defect, whereby the defect is removed without applying a chemical etchant.

In another embodiment of present invention, the improved method of detecting and removing an electrical defect from a photoelectric semiconductor device comprises the steps of characterizing the device by generating actual electrical performance data; forward biasing the device; producing electromagnetic radiation from the device; receiving the radiation; associating a contrast in radiation to the defect; and mechanically removing the defect, whereby the defect is removed in the absence of a step of applying a chemical to the defect to assist in removing the defect. The cell is then re-tested electrically to determine if the shunt(s) have been adequately removed.

In yet another embodiment of present invention, the improved system for detecting and removing a shunt from a semiconductor device comprises a power supply that can supply a voltage to the device; a light detector that can detect emitted light from the device upon a voltage being supplied to the device; a monitor that can produce a contrast in emitted light from an examination area of the device such that the contrast can be used to identify the shunt; and a mechanical removal means for mechanically removing the shunt upon the shunt being identified, whereby the shunt is removed in the absence of a chemical etchant being applied to the shunt and that assists in removing the shunt.

These and other features, aspects and advantages of the present invention will become better understood with reference to the following drawings, description, and claims.

DESCRIPTION OF THE PREFERRED EMBODIMENTS

In general, the present invention provides a method of shunt detection and removal, as well as apparatus for practicing such method. But while the method and apparatus of the present invention are described in the context of shunts, the invention is not so limited. Accordingly, the present invention may be used to detect and remove electrical defects in general, including electrical shorts. Further, even though the present invention can be particularly useful for photovoltaic cells, it is contemplated that the invention can be practiced with semiconductor devices in general that can emit electromagnetic radiation. As an example, the invention can be practiced with light emitting diodes, laser diodes, integrated circuits and other semiconductor devices such as power transistors. Furthermore, even though the present invention is described in the context of photovoltaic cells that can be incorporated into a solar panel 51 of a spacecraft or satellite 50, the invention can be applied in other environments.

Figure 1:
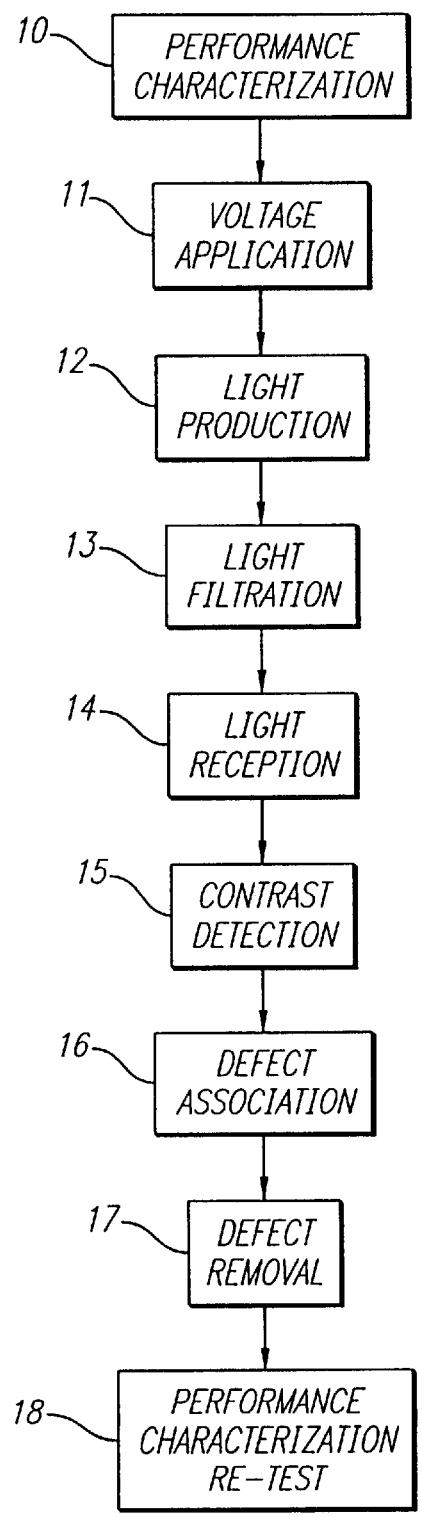
FIG. 1 is a flowchart depicting the steps or acts of shunt detection and removal according to an embodiment of the present invention.

FIG. 1 is a flowchart that depicts the general steps or acts of a method according to the present invention for detecting and removing a shunt of a photovoltaic (PV) cell, for example. Generally, the PV cell will first undergo a step or act 10 that includes characterizing the performance of the cell by initial actual performance data that is preferably in the form of an initial actual performance graph. The performance graph is preferably a current versus voltage graph or, in other words, an I–V curve. Well known test equipment, such as Spectrolab X-25 Steady State Solar Simulator System can be utilized to provide the initial performance data and/or graph.

Figure 2:
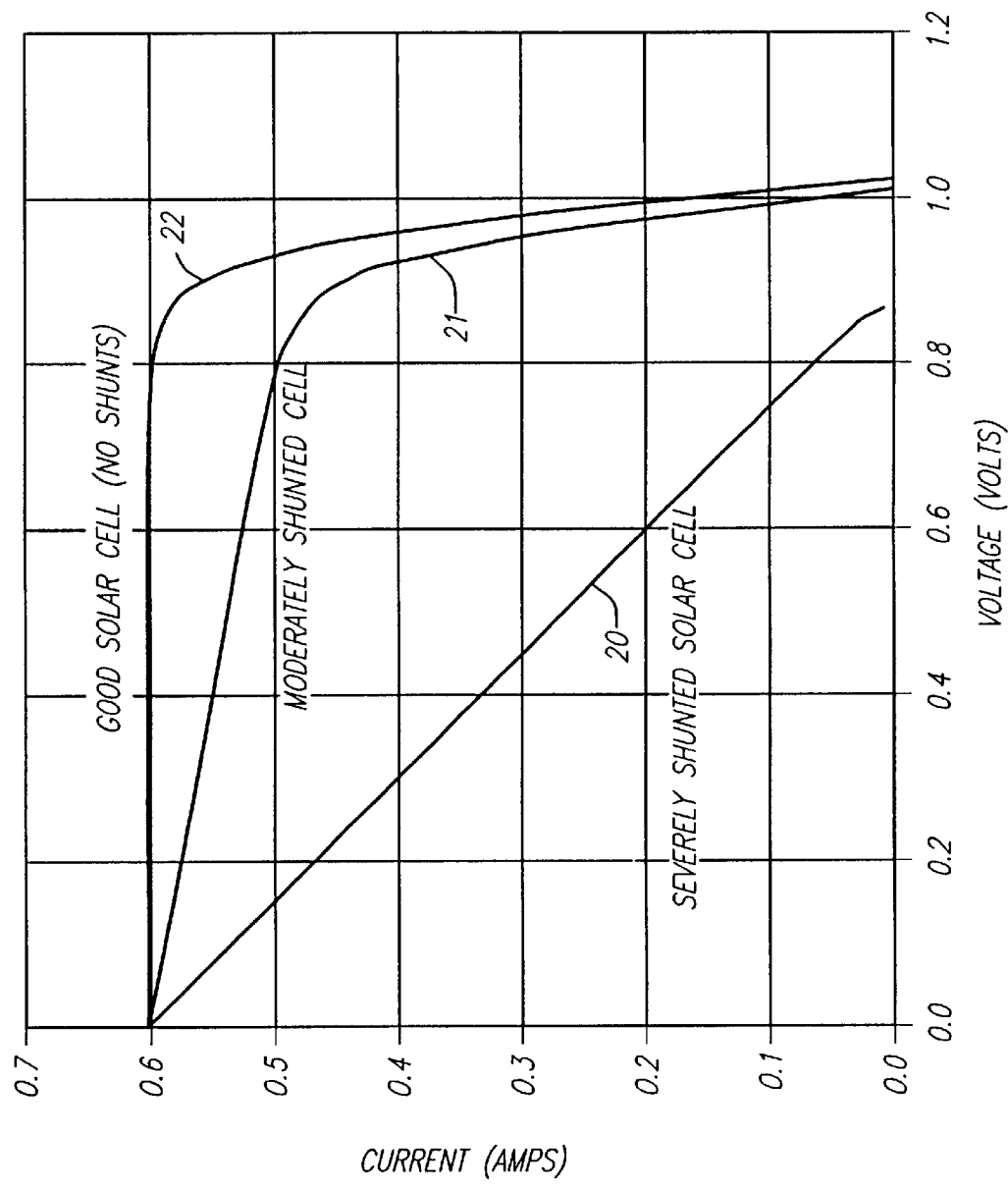
FIG. 2 is graph of current versus voltage for an illustrative non-shunted cell, a moderately shunted cell, and a severely shunted cell.

For purposes of illustration, FIG. 2 depicts I–V curves 20,21,22. The curve 20 is intended to illustrate what a severely shunted device might produce. The curve 21 is intended to illustrate what a moderately shunted device might produce. The curve 22 illustrates the performance of a non-shunted or insignificantly shunted device. In essence, the curves 20–22 represent standard performance graphs of what is desired and undesired device performance. A device can then be initially performance tested to provide an initial actual performance graph that can then be compared to the standard performance graphs and/or standard performance data that can include allowable specification parameters for voltage, current and diode characteristics.

If, upon comparison, the initial actual performance graph is not similar to the desired performance graph 22 (and/or standard performance data), but is similar to either the severely shunted graph 20 or the moderately shunted graph 21, the device can then undergo a step or act 11. Alternatively, the PV cell may be completely rejected such that the remaining steps described hereinafter are not completed. The step 11 includes applying a voltage to forward bias the device. The forward biasing of the device leads to a step or act 12 which involves producing electromagnetic radiation from the device. In the specific context of a PV cell, the emitted radiation will be in the form of light, either visible or infrared, depending on the bandgap of the material. For other materials and devices, a high frequency wave can be produced, such as microwave or radar.

Upon the device producing or emitting radiation, a step or act 13 can occur. The step 13 includes filtering the produced light or wave. In other words, if the device includes more than one semiconductor layer or cell, such as in a multi-function PV cell, each layer or cell will radiate light at a respective wavelength range. By sequentially filtering the light for each wavelength range, the radiation from each layer or cell can be substantially isolated from the others in a sequential fashion. Doing so allows each layer or cell to be individually and sequentially examined for the presence of undesired shunts, as further described below.

As the radiation from each cell of the device is isolated, a step or act 14 of light reception occurs. For example, a light detector, such as an infrared camera 42 in the case of a photovoltaic cell, receives the radiation. During the step 14 of receiving light, the light can be restricted to an examination area of the device, namely a portion of the layer or cell that is radiating the light. Within the examination area, and assuming there is at least one shunt, there will be at least one area having one brightness and another area having a second brightness. This contrast in brightness or radiation allows a step or act to occur.

The step 15 includes the detection of a contrast in brightness or radiation within the examination area, such as by a video monitor 44. After step 15 occurs, a step or act 16 can occur. In step 16, the contrast in radiation is associated with a defect or shunt. A non-shunted portion of the layer's examination area will typically appear bright, while a shunted portion will typically appear dark and in the form of a spot. Notwithstanding the foregoing, it can be understood that depending upon the particular filters used for filtering the electromagnetic radiation, as described above, a shunted portion can also appear as a lighter contrasting area. Using filters will also make the intensity invert on other layers. Further, a larger shunt will appear as a larger dark spot. Therefore, the present invention allows for selective shunt removal based on the size and severity of the shunt.

Next, a step or act 17 takes place and includes mechanically removing the defect or shunt. In particular, the step 17 obviates the need or use of a chemical, such as an etchant, applied to the defect to assist in its removal. Accordingly, the step 17 can be carried out by manually scraping with a sharp tool, ablation with a laser, microblasting through a mask using abrasive microparticles, and high speed grinding or drilling. Suitable mechanical removal means include a blade, a dental probe, a laser, and a high speed drill or grinder. By such mechanical removal means, the shunt is mechanically removed during the step 17, as the material of the cell that contains the shunt is mechanically removed. The material of the cell that is removed can include a metal grid. And during such removal, it is not necessary that the removed material be limited to the particular layer of cell that contains the defect. Accordingly, the material may be removed from the top of the device and down into substrate without a noticeable loss in performance.

Figure 3:
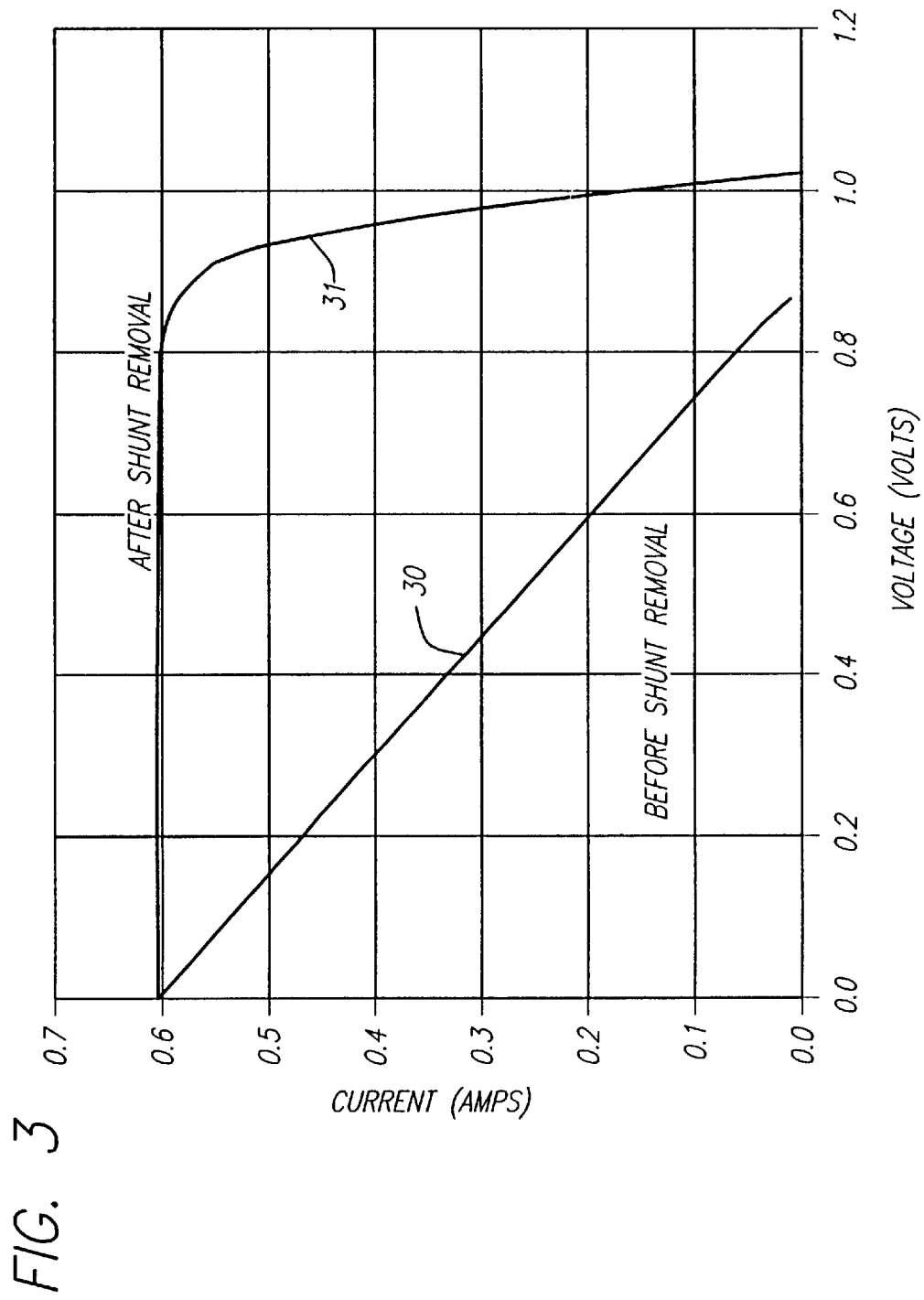
FIG. 3 is graph current versus voltage for an illustrative shunted cell and after the shunted cell has been subjected to the method according to the present invention.

During a step or act 18, the device is performance re-tested with the test equipment used in step 10 for current and voltage electrical data. In referring to FIG. 3, curve 30 illustrates what the initial actual performance curve (or data) of the device may have been prior to the device undergoing the steps of the present invention. The curve 31 illustrates the subsequent actual performance curve (or data) of the device after undergoing the method of the present invention. Steps 10 through 18 may be repeated, as needed to produce a curve 31 at step 18.

Figure 4:
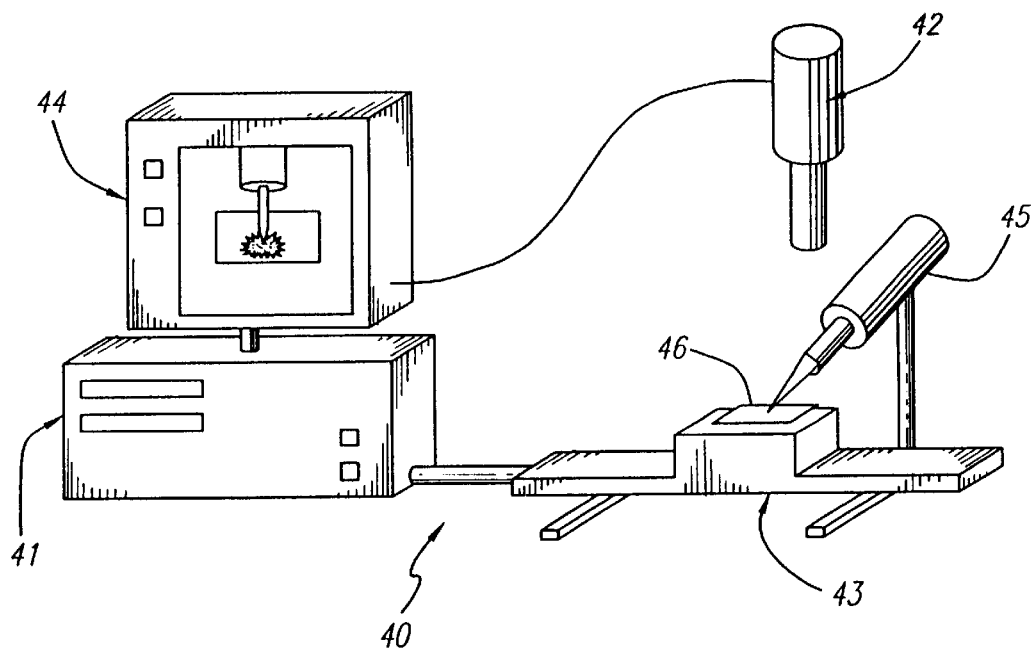
FIG. 4 is a view of a shunt detection and removal system according to an embodiment of present invention.
Figure 5:
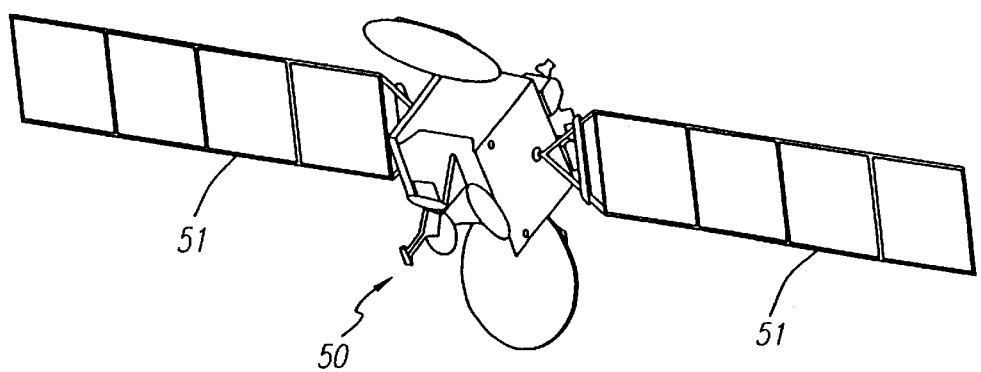
FIG. 5 is a perspective view of a satellite on which a photovoltaic cell has been subjected to the shunt detection and removal method of the present invention.

To carry out the steps of the present invention, FIG. 4 depicts a shunt detection and removal system 40. The system 40 includes a combined power supply and central processing unit (CPU) 41. The power supply 41 can provide a voltage to a PV cell 46 that is supported by a base 43. Upon the cell 46 being forward biased, the cell emits infrared and visible light in this case that can be received by the camera 42. The received light can then be viewed on the video monitor 44. Upon a shunt being detected, the CPU 41 can control the position of the cell 46 via the base 43 that is moveable in two orthogonal directions. With the support being so moveable, the CPU 41 can position the shunt for removal by a high-speed grinder 45 or other mechanical means as described earlier. Optionally, the CPU 41 can position the cell 46 for performance testing by the test equipment. A z-axis operation of the high-speed grinder 45 is also controlled by the CPU 41.

As can be appreciated by those skilled in the art, the present invention provides a method of improving the performance of a semiconductor device and minimizing the potential for scrap material in growing such device. The present invention also provides a method of detecting and then removing electrical defects from semiconductor devices, including multi-junction and/or single junction photovoltaic cells. The method of the present invention also selectively identifies which of a number of shunts require removal and then removing only those needed to be removed. The present method also provides for the removal of shunts that can exist under a metal grid or others that are not susceptible to chemical removal.

It should be understood, of course, that the foregoing relates to preferred embodiments of the invention and that modifications may be made without departing from the spirit and scope of the invention as set forth in the following claims.

What is claimed is:

1. A method of detecting and removing an electrical defect from a semiconductor device, comprising the steps of:

producing electromagnetic radiation from said device;

receiving said radiation;

detecting a contrast in radiation;

associating said contrast to said defect; and mechanically removing said defect, whereby said defect is removed in the absence of a step of applying a chemical to said defect that assists in removing said defect.

2. The method of claim 1, further comprising the step of characterizing said device by performance data prior to the step of producing electromagnetic radiation.

3. The method of claim 1, further comprising the step of forward biasing said device prior to the step of producing electromagnetic radiation.

4. The method of claim 1, further comprising the step of filtering said radiation prior to the step of receiving said radiation.

5. The method of claim 1, further comprising the step of sequentially receiving radiation from a plurality of semiconductor layers in said device.

6. A method of detecting and removing an electrical defect from a photoelectric semiconductor device, comprising the steps of:

characterizing said device by initial actual performance data;

forward biasing said device;

producing electromagnetic radiation from said device;

receiving said radiation;

associating a contrast in radiation to said defect; and mechanically removing said defect in the absence of a step of applying a chemical to said defect that assists in removing said defect; and re-characterizing said device by subsequent actual performance data.

7. The method of claim 6, further comprising the step of comparing said initial and subsequent actual performance data to standard performance data.

8. The method of claim 6, wherein said actual performance data comprises a current versus voltage graph.

9. The method of claim 6, further comprising the step of isolating said radiation to a single semiconductor layer in said device prior to the step of receiving said radiation.

10. The method of claim 6, wherein the step of receiving radiation comprises the step of receiving radiation from substantially only one of a plurality of semiconductor layers in said device.

11. The method of claim 6, further comprising the step of detecting a contrast in radiation within an examination area of said device.

12. The method of claim 6, further comprising the step of determining whether an examination area of said device includes a difference in intensity between a first area and a second area.

13. The method of claim 6, wherein the step of mechanically removing comprises the step of subjecting said defect to one of the steps of scraping, grinding, microblasting, lasing and cutting.

14. A method of detecting and removing a shunt from a photovoltaic cell, comprising the steps of:
characterizing performance of said device by an actual performance graph of current versus voltage;
applying a voltage to said device to forward bias said device;
producing electromagnetic radiation from said device;
receiving said electromagnetic radiation;
determining whether said electromagnetic radiation includes a difference in intensity between a first area and a second area;
associating one of said first area and second area to said shunt;
removing said shunt in the absence of a chemical that can assist in removing said shunt; and
re-characterizing said device by a subsequent actual performance graph of current versus voltage.

15. The method of claim 14, wherein said photovoltaic cell can be used in a solar panel of a spacecraft.

16. The method of claim 14, further comprising the step of comparing said initial and subsequent actual performance graphs to a plurality of standard performance graphs of current versus voltage.

17. The method of claim 14, further comprising the step of providing a camera to receive said electromagnetic radiation.

18. The method of claim 14, wherein said photovolatic cell comprises a plurality of semiconductor layers.

19. The method of claim 18, further comprising the step of isolating said electromagnetic radiation by wavelength to substantially only a single semiconductor layer of said photovoltaic cell.

20. The method of claim 14, further comprising the step of examining said electromagnetic radiation within an examination area of said photovoltaic cell.

21. The method of claim 20, wherein said examination area comprises said first and second areas.

22. The method of claim 14, wherein the step of associating comprises the step of assigning one of a lighter area and a darker area in said first and second areas to said shunt.

23. The method of claim 14, wherein the step of removing comprises the step of subjecting said shunt to a mechanical removal process.

24. A system for detecting and removing a shunt from a semiconductor device, comprising:

a power supply that can supply a voltage to said device;
a detector that can detect emitted electromagnetic radiation from said device upon said voltage being supplied to said device;
a monitor that can monitor a contrast in emitted electromagnetic radiation from an examination area of said device such that said contrast can be used to identify said shunt; and
a mechanical removal means for mechanically removing said shunt upon said shunt being identified,
whereby said shunt is removed in the absence of a chemical being applied to said shunt and that assists in removing said shunt.

25. The system of claim 24, further comprising a base that can support said device while said emitted electromagnetic radiation is being monitored by said monitor and said shunt is being removed by said removal means.

26. The system of claim 25, wherein said base is moveable in two orthogonal directions.

27. The system of claim 24, wherein light detector comprises a camera and filters.

28. The system of claim 24, wherein said removal means is selected from the group consisting of a blade, a microblaster, a laser, and a grinder, and said removal means is moveable in a z-axis.

29. The system of claim 24, further comprising test equipment for determining actual performance data of said device.

30. A system for detecting and removing a shunt from a photovoltaic cell that can be used on a spacecraft, comprising:
a base for supporting said cell;
a power supply that can supply a voltage to forward bias said cell;
a camera that can detect visible and infrared light from said cell upon said cell being forward biased;
a video monitor that can monitor contrasting areas of light emitted from an examination area of said cell such that said contrasting areas can be used to identify said shunt;
a mechanical removal means for mechanically removing said shunt; and
a central processing unit that is capable of determining said contrasting areas of light, controlling the operation of said mechanical means, and controlling a position of said base.

31. The system of claim 30, wherein said support is moveable in two orthogonal directions.

32. The system of claim 30, wherein said contrasting areas of light comprise a first area described by a first brightness and a second area described by a second brightness.

33. The system of claim 32, wherein said central processing unit is further capable of distinguishing whether the first brightness is brighter or dimmer than the second brightness.

34. The system of claim 30, wherein said mechanical removal means is one of a blade, drill, laser, and grinder.

35. The system of claim 30, further comprising test equipment for determining actual performance data of said cell.

* * * * *